(12) United States Patent
Ekberg et al.

(10) Patent No.: US 6,585,898 B1
(45) Date of Patent: Jul. 1, 2003

(54) METHOD AND APPARATUS FOR PREPARATION AND USE OF OZONE WATER

(75) Inventors: Kjell Ekberg, Vaxholm (SE); Sudhir Chowdhury, Farsta (SE)

(73) Assignee: Otre AB, Solna (SE)

( * ) Notice: Subject to any disclaimer, the term of this patent is extended or adjusted under 35 U.S.C. 154(b) by 0 days.

(21) Appl. No.: 09/623,834

(22) PCT Filed: Mar. 2, 1999

(86) PCT No.: PCT/SE99/00298

§ 371 (c)(1),
(2), (4) Date: Nov. 17, 2000

(87) PCT Pub. No.: WO99/46201

PCT Pub. Date: Sep. 16, 1999

(30) Foreign Application Priority Data

Mar. 9, 1998 (SE) ................................................ 9800751

(51) Int. Cl.[7] ................................................. C02F 1/78
(52) U.S. Cl. ...................... 210/760; 210/739; 210/764; 210/765; 210/101; 210/192; 210/194; 210/205
(58) Field of Search ................................ 210/739, 760, 210/764, 765, 101, 192, 194, 198.1, 205

(56) References Cited

U.S. PATENT DOCUMENTS

| 3,731,522 A | | 5/1973 | Mikesell |
|---|---|---|---|
| 5,324,666 A | | 6/1994 | Siepmann et al. |
| 5,510,060 A | * | 4/1996 | Knoll |
| 6,001,247 A | * | 12/1999 | Schulz |
| 6,030,586 A | * | 2/2000 | Kuan |
| 6,068,778 A | * | 5/2000 | Steiner et al. |
| 6,146,524 A | * | 11/2000 | Story |
| 6,405,900 B1 | * | 6/2002 | Kown |

FOREIGN PATENT DOCUMENTS

| DE | 4305227 C1 | 8/1994 |
|---|---|---|
| EP | 0605277 A1 | 7/1994 |
| JP | 4172243 | 6/1992 |
| JP | 9122214 | 5/1997 |

* cited by examiner

*Primary Examiner*—Betsey Morrison Hoey
(74) *Attorney, Agent, or Firm*—Young & Thompson

(57) ABSTRACT

A system for production of water having dissolved ozone includes a water feeding section, a container part, an ozone feeding part for feeding ozone to a mixing part dissolving ozone in the water, the mixing part drawing water from the lower part of the container, an ozone measuring part for measuring the ozone concentration of the water in the container, a water pump for circulating the water from the lower part to an upper part of the container in dependence of the measured ozone concentration and from the ozone feeding section to the mixing part in dependence of a predetermined ozone concentration, the container having an outlet for water having the predetermined concentration of ozone.

19 Claims, 11 Drawing Sheets

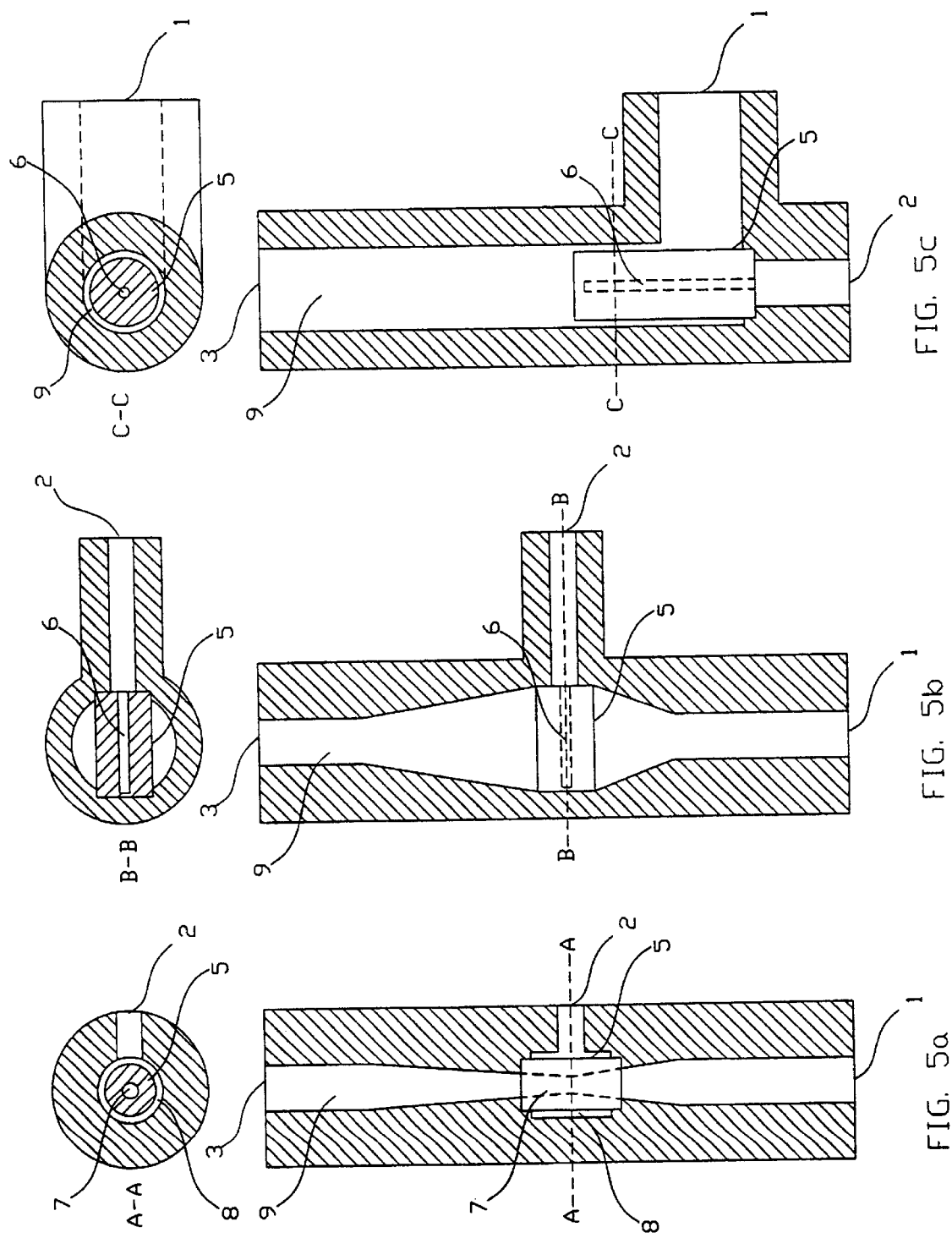

METHOD AND APPARATUS FOR PREPARATION AND USE OF OZONE WATER

As the population in the world grows and as the movements of people increases the amount of viruses and micro-organisms also increases. We all come into contact with at least some of these during our daily lives. These contacts result in illness and even causes death.

For long time the use of chlorine and derivatives thereof, as disinfectant, has prevailed. During later years drawbacks have been noted in connection with the use of chlorine and related compounds.

Ozone has been used for disinfectant purposes. It has a strong oxidizing effect on materials coming into contact with the ozone and is very effective as a bactericide even when used against the most resistant bacteria and virus species e.g. listeria, MARS and *escherichia coli* etc. Thus chlorine and other dangerous and poisonous disinfectants may be replaced.

In EP,A2,0712634 is disclosed a system for treating and sterilization of biological, solid, etc hospital residues, in which residues are grinded and treated with a mixture of oxygen+ozone+carbon dioxide+water//oxygen+ozone+water. The system is designed to dissolve the gaseous components in the water and the mixing system moves the water into an absorption and de-gasification tank whereafter the water plus the gases are put into the washer which contains the material to be sterilized. The crushed residuals are then subjected to a continuos bath with permanent recirculation with the water mix. The gases are mixed with the water in increasing amounts in the separate parts of the system.

In RU,C1,2068263, is described how to treat wounds with ozone in order to speed up the healing process.

A device for increasing the intensity in the spraying of ozone is described in DE 3215371.

A device for medical treatment using ozone is described in EP,A1,0,450,103, in which during the treatment the part of the body which is to be treated with ozone gas is trust into a sealed container where the ozone is allowed to pass through the sealed portion.

Devices for making steam having an admixture of ozone are know e.g. from FR,A,2484279.

Herein below the following words are used:

Ozone-water—A water-ozone solution (also termed Active water), which is a sterile water rich in ozone. The Ozone -water may optionally contain oxygen.

A specific problem as regards the use of ozone is the relative instability of the same compared to oxygen. Ozone spontaneously decays to oxygen with a half life of 3 days at 20° C., 8 days at −15° C., which show the temperature dependence of the decay. These figures refers to the gas. These data are cited from Römpp, Chemie Lexicon, Thieme, Band 7, 1991.

Ozone is a highly reactive and as such harmful to materials and living matter. Therefore locations in which ozone is manufactured or is evolved as a by-product of some machinery or chemical reaction must be well ventilated on account of the harnfuil effects caused by the gas.

The aim of the invention is to be able to use ozone in a safe and predictable way in different applications.

It is also an aim of the present invention to generate ozone-water in a safe and reproducible way, giving a controlled gas and water flow.

It is also an aim of the invention to generate this ozone-water in predetermined concentrations, also insuring a controlled temperature and pressure of the solution.

A further aim is to accomplish an optimal solubility of the ozone gas in the water A further aim of the invention is a system for accomplishing the above aims Yet another purpose is a device for administering the ozone-water in the form of a spray or in liquid form.

Yet another purpose is to produce ozone and ozone-water of the purest quality.

Yet a further object is to combine the system with various means for treatment.

These and other objects, advantages and features of the present invention will be more readily understood from the following detailed description of the preferred embodiments thereof, when considered in conjunction with the drawings, in which like reference numerals indicate identical structures through the several views, and wherein.

Figure 4B:
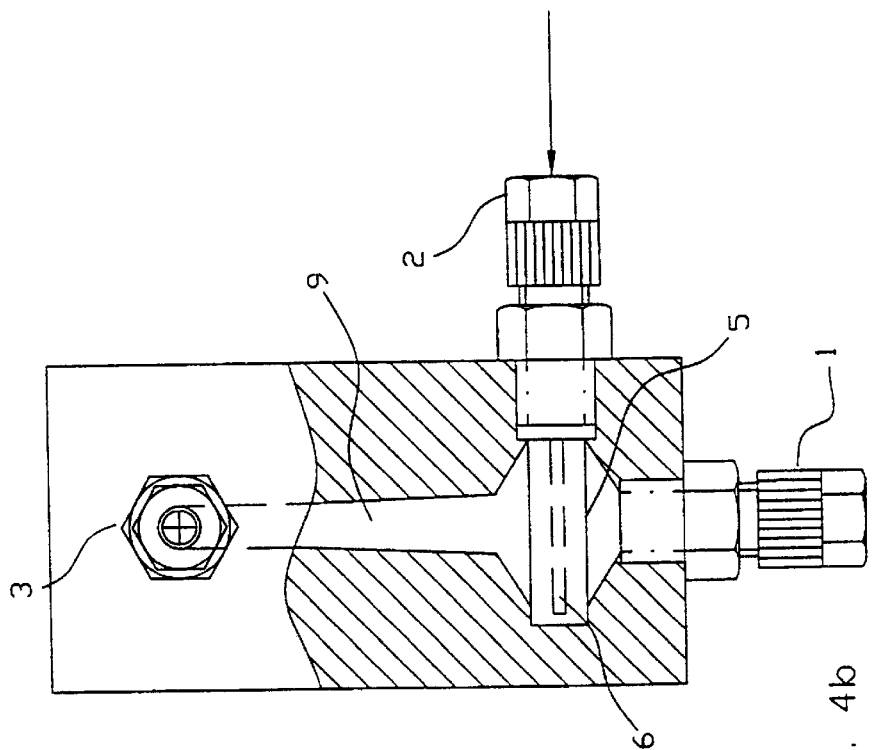
Figure 4A:
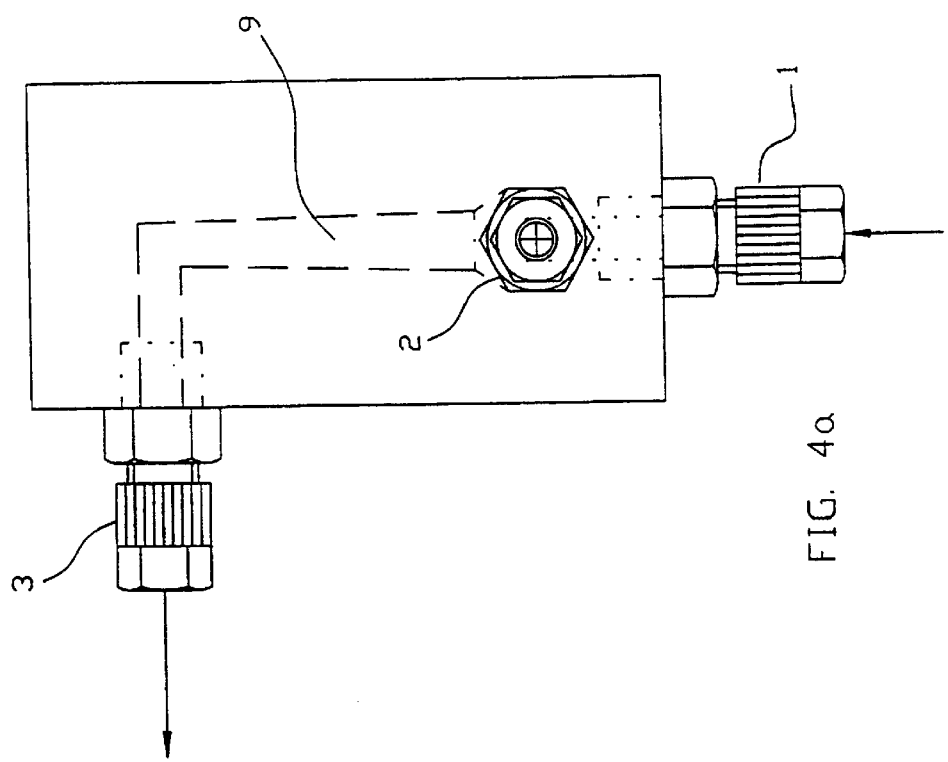

FIGS. 4a and b shows on embodiment of a mixing chamber according to the invention.

FIGS. 5a, b, c shows a second, a third and a fourth embodiment of a mixing chamber according to the invention.

Figure 6:
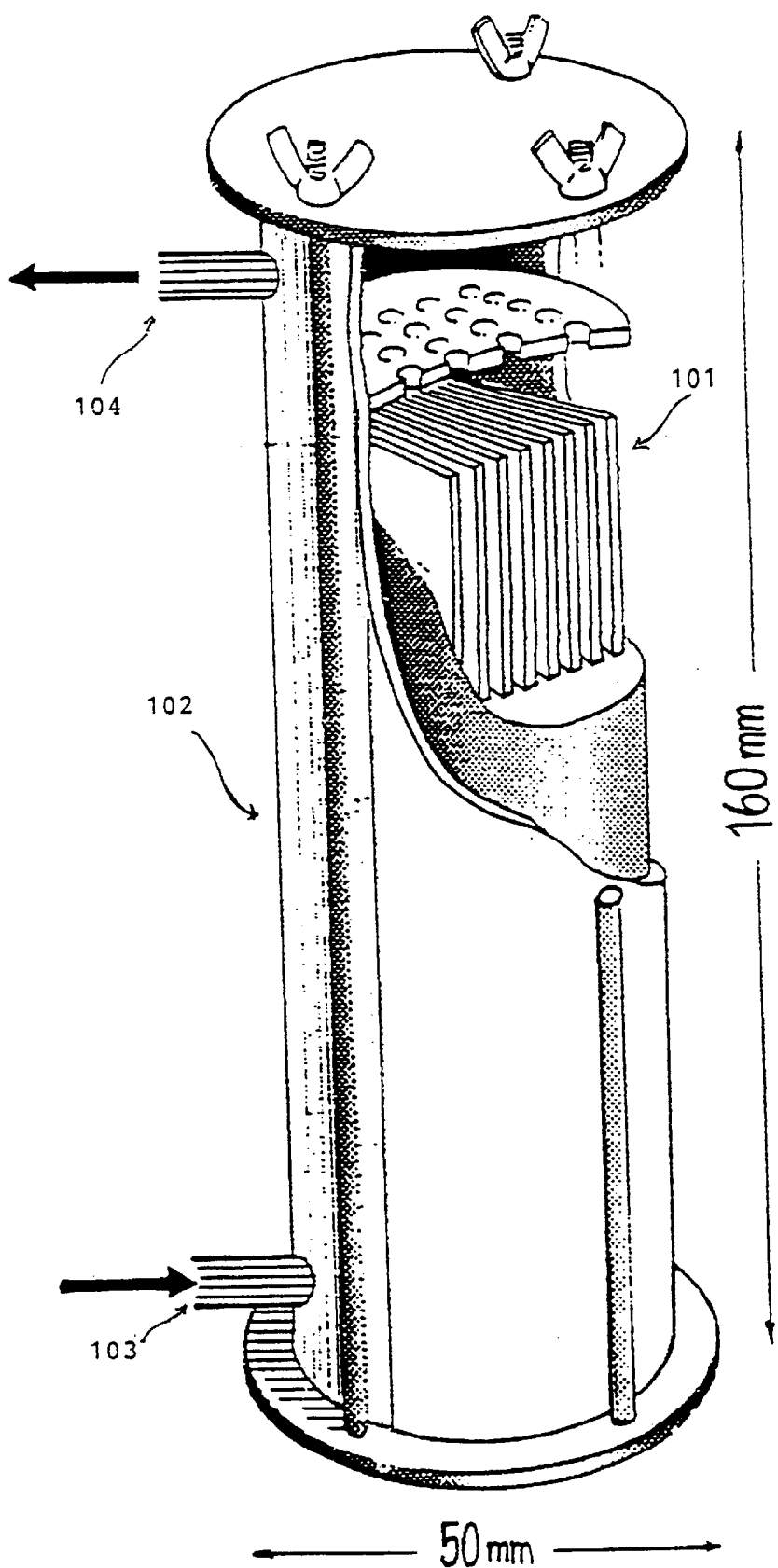

FIG. 6 shows a flow-cell used in experiments for assessing the effect of the method according to the invention.

Figure 7A:
Figure 7B:
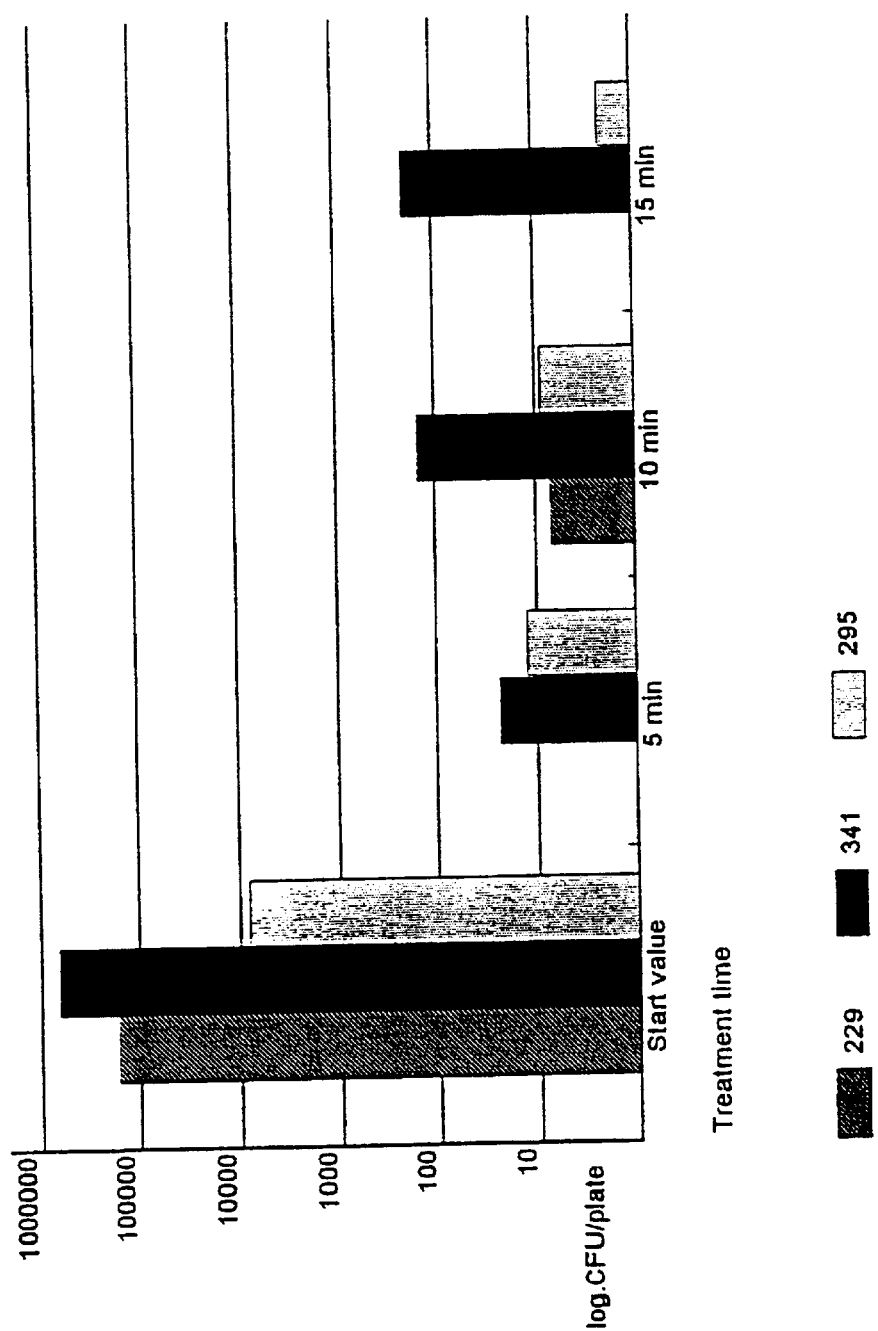

FIGS. 7a and 7b show the results of experiments made using equipment and method according to the invention.

Figure 8:
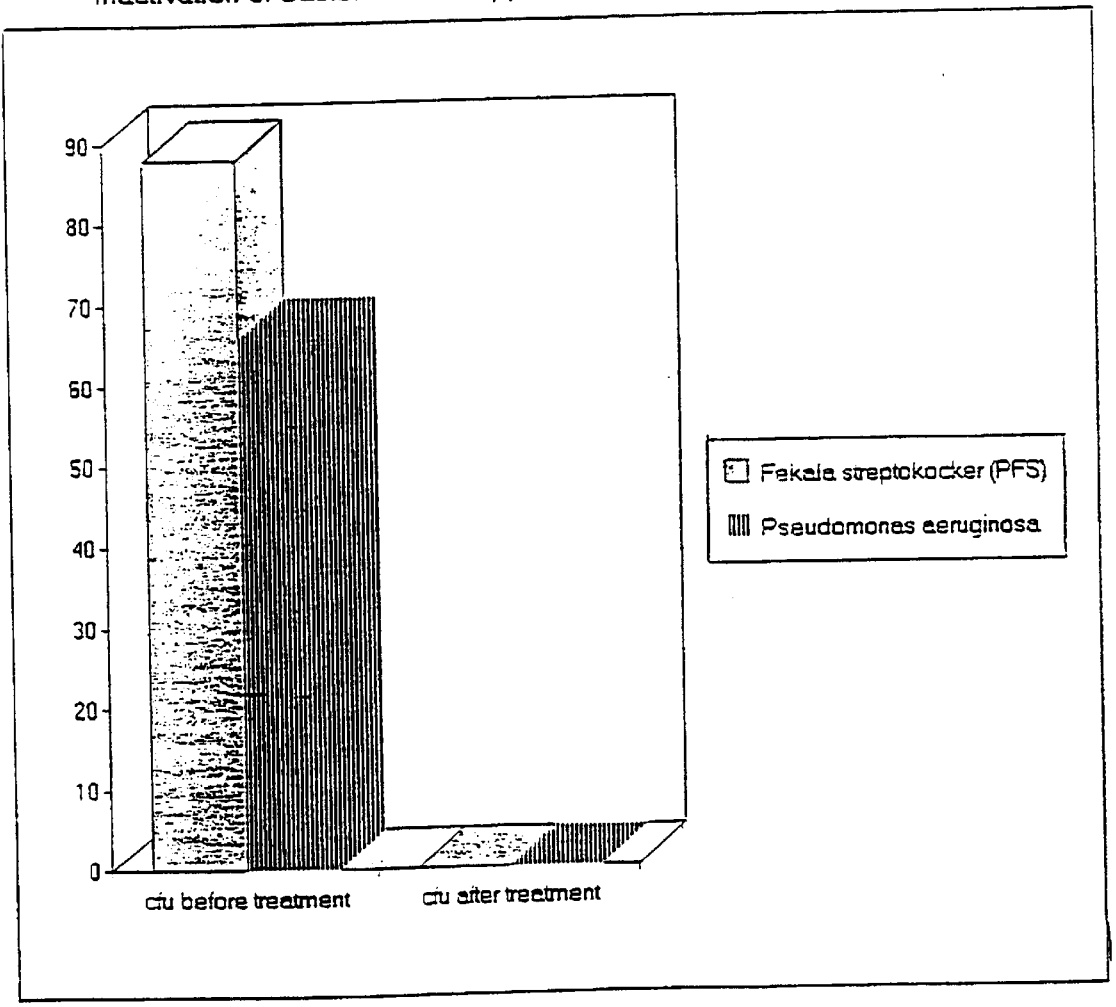

FIG. 8 shows the results of another experiments made using ozone-water solution and method according to the invention.

Figure 9:
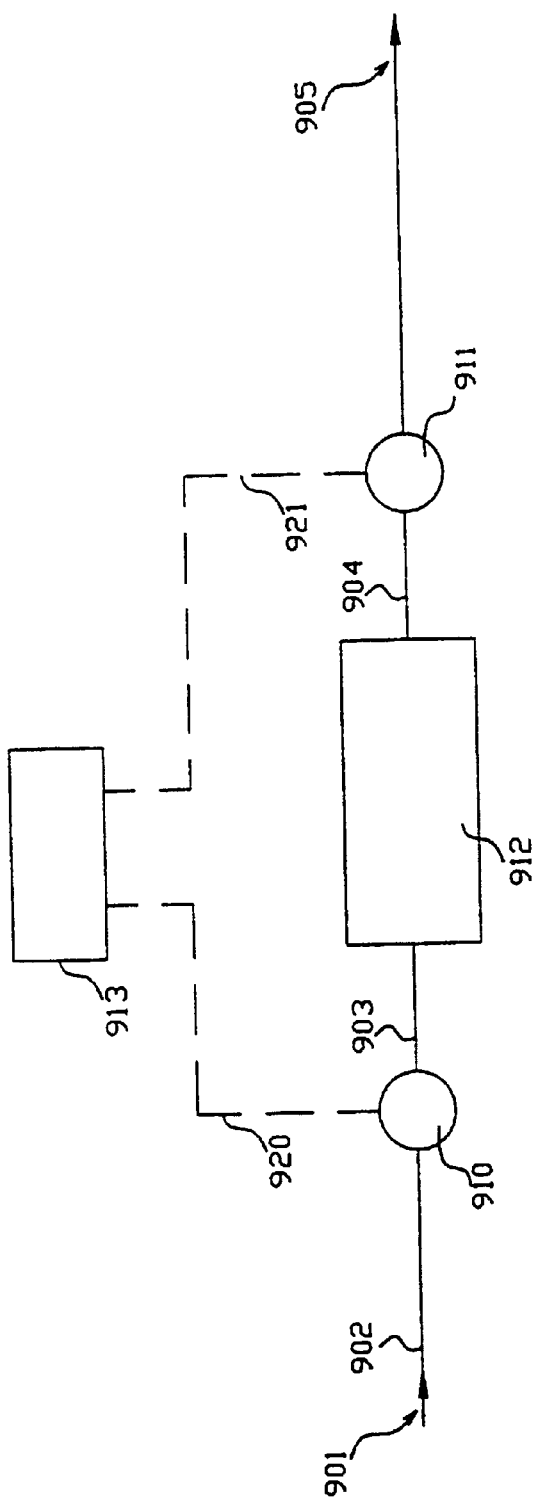
Figure 10:
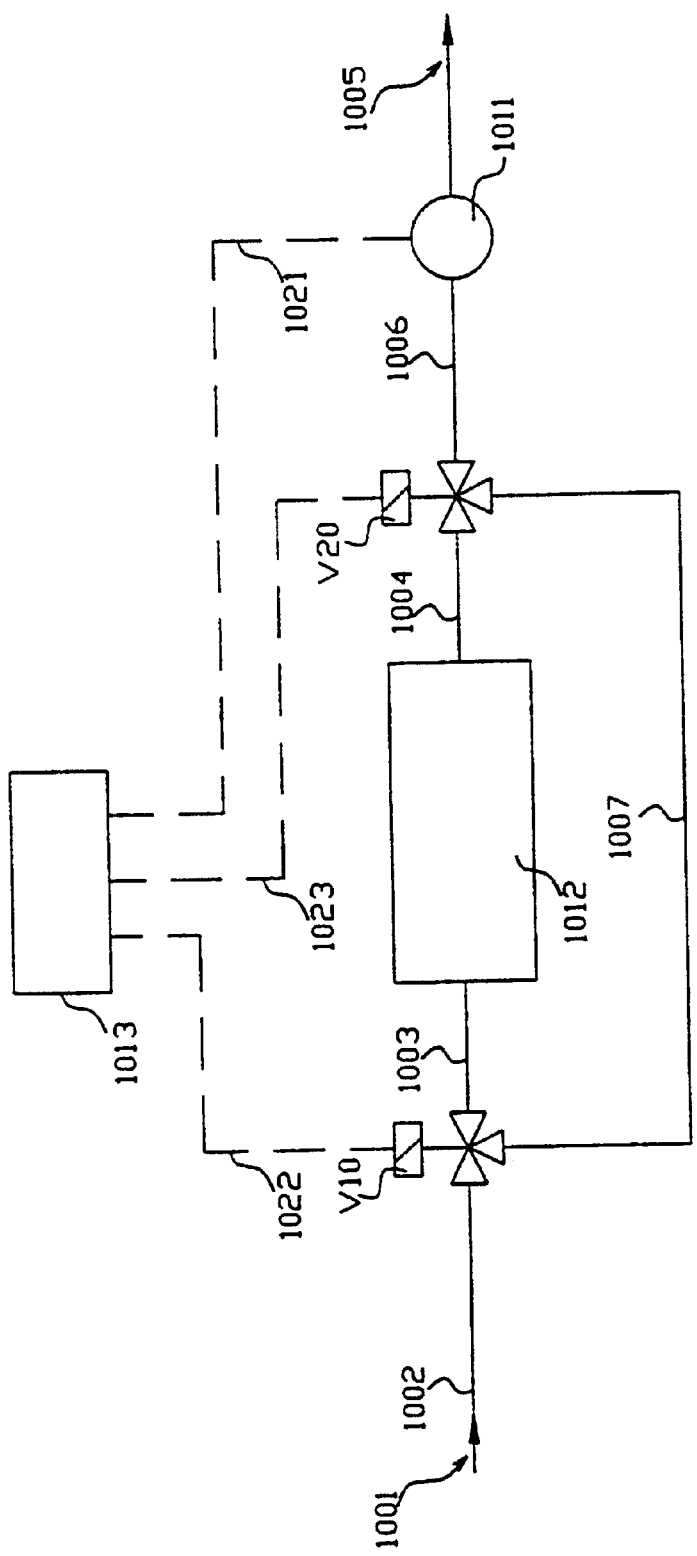

FIGS. 9 and 10 shows two embodiments of a purification and/or analyse part system to be used in conjunction of to be integrated with the system according to the invention.

DETAILED DESCRIPTION OF THE PREFERRED EMBODIMENTS OF THE INVENTION

Figure 1:
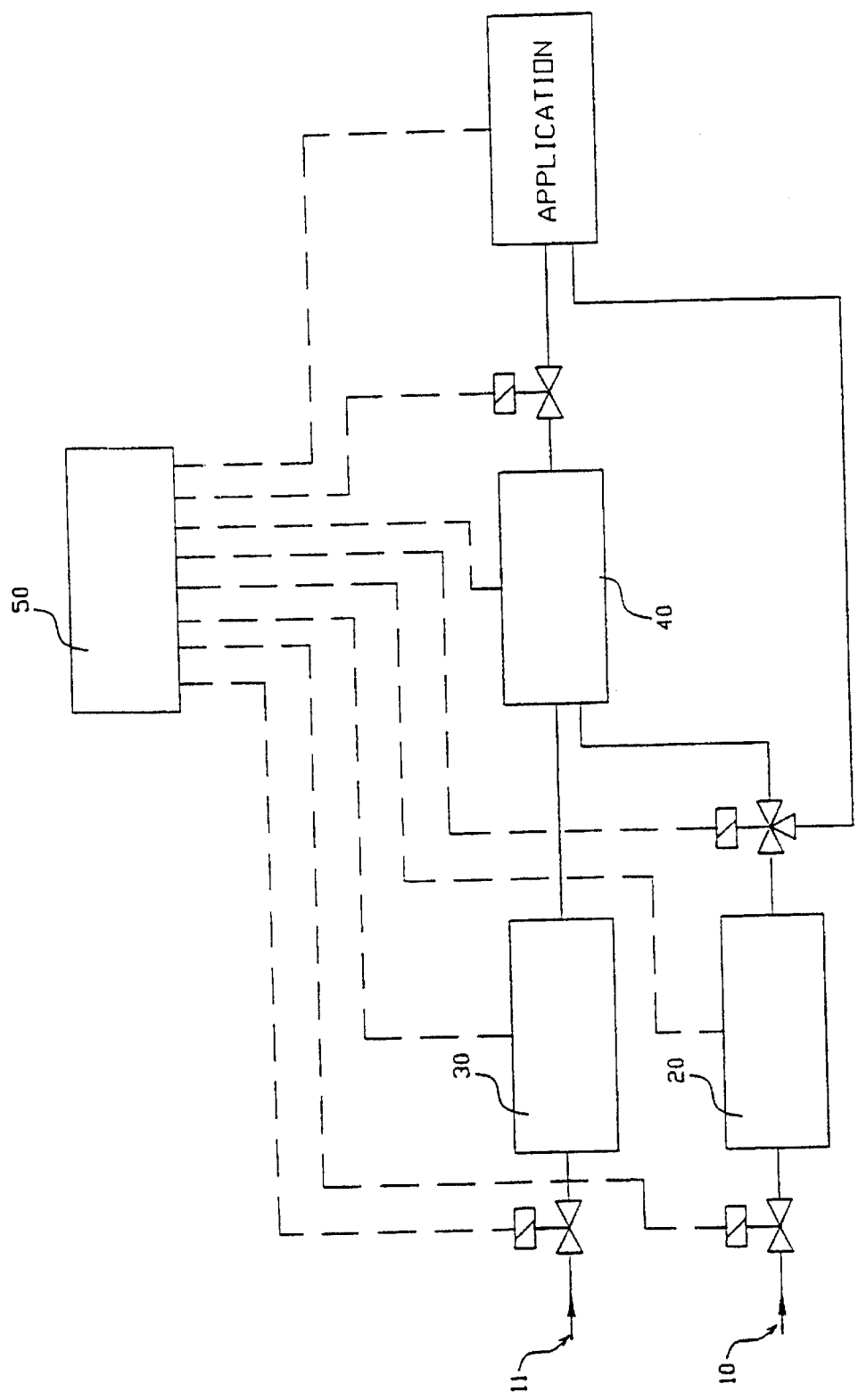
FIG. 1 shows an over-all view of one embodiment o the system according to the invention

In FIG. 1 is shown the general principle represented by one embodiment of a system according to the invention. The system of this embodiment comprises an inlet 10 for oxygen/air, an inlet 11 for water, a unit 20 for generation of ozone, a unit 30 for treatment of incoming water, a mixing unit 40, a PLC control system 50, controllable valves and conduits, and leads connecting the valves and the control system 50. The incoming water is filtered, de-mineralised, and separated into two or more water fractions in the unit 30 for treatment of incoming water and thereafter used in the mixing unit 40. The incoming air/oxygen is treated in the ozone generator unit 20 and thereafter sent to the mixing unit 40 to be mixed with the treated water. After the mixing unit the ozone-water may be saved temporarily in a dissolution tank, below tank (not shown), or used directly or the ozone may also be used directly.

A further description of the conduits and valves is given below in connection with a more detailed description of the system as such, in FIG. 2 and the control system in FIG. 3.

Figure 2:
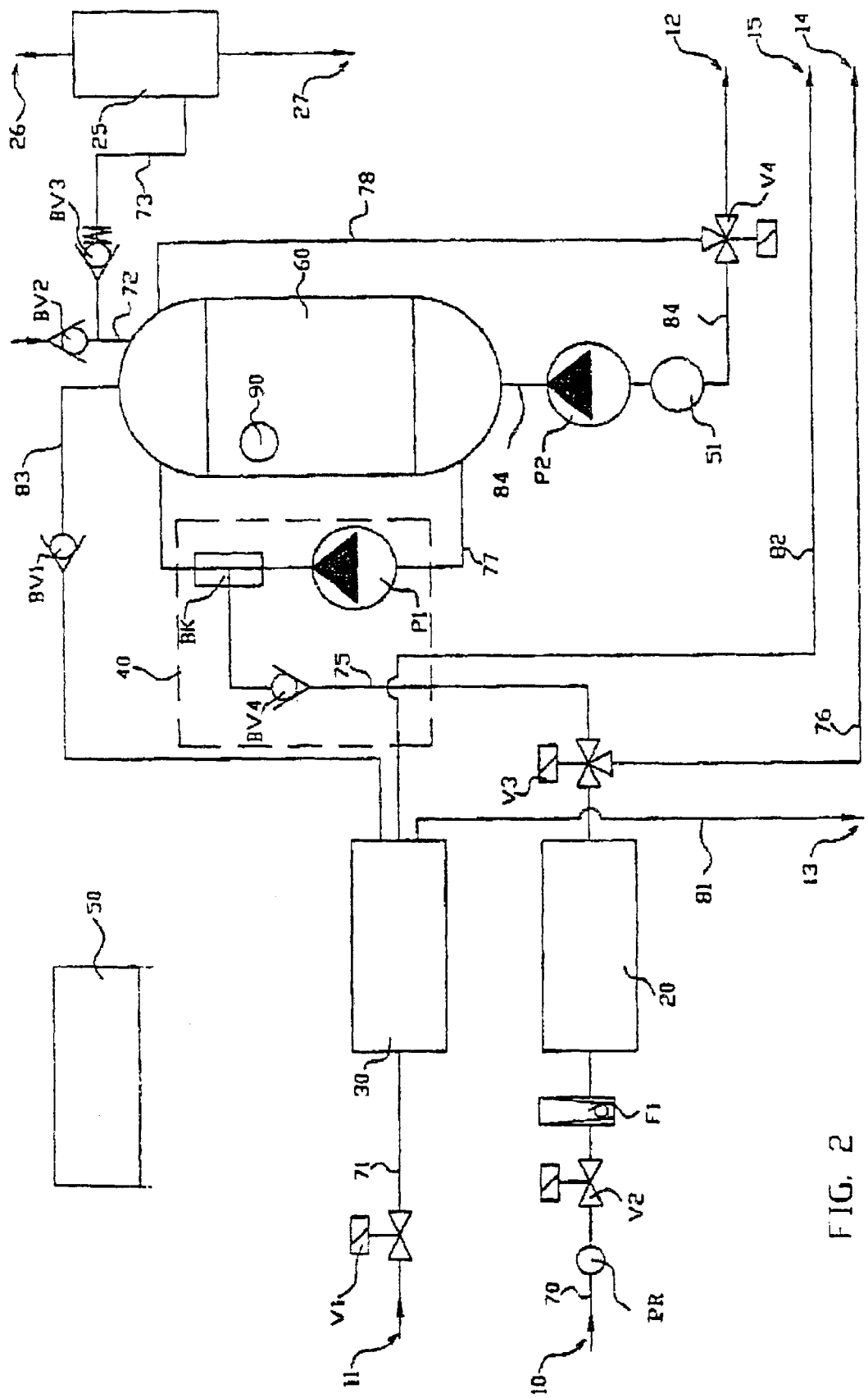
FIG. 2 shows a schematic overview of the conduits, valves, tank, etc. of one embodiment of the invention according to the invention.

Referring now to FIG. 2, in which an embodiment of the system for producing ozone-water, ozone (active water) according to the invention is shown. The system comprises an inlet conduit 71 for water in which conduit a controlled reducing valve V1, e.g. a magnetic valve, is arranged, following that a unit 30 for treatment of incoming water, filtering and de-ionising (de-mineralising) and separation into two fractions exhibiting two different pH-values, an inlet conduit 70 for air or oxygen gas to the ozone generator 20, which may be a commercial ozone generator of a type which produces the necessary ozone, e.g. Plasma Resonance Electron, Ozonice, Japan.

The electrolysis chamber in the unit 30 should be rinsed at intervals and is drained via a separate drain conduit 81 to an outlet 13. A temperature regulating function may be built in at/or near the unit 30.

In the conduit 70 a controlled valve V2, a pressure sensor PR and a flow sensor F1 are arranged.

The unit for filtering and de-mineralising is electically controlled and mechanically adjusted. The pH-value of the water is adjusted by dividing the water into at least two fractions using e.g. an apparatus as described above. Such apparatus are commercially available e.g. an alkaline ionizer, Bion Q Water Ionizer from DAE-A Medical Ltd.

The adjustment of the water may be performed in one step or in several steps depending on the quality of the war that is used as input in the system. The water flows via conduit 83, through a check valve BV1 to a tank 60. The treated water is fed to the tank 60 in which there is aged a liquid level indicator 90. There may of course be arranged more than one liquid level sensor e.g. one for the maximum level and one for the minimum level.

From the unit 30 for treatment of the incoming water there are two more outlets. One outlet 13 is a drain for surplus water or the like which is drained through a conduit 81, and also a conduit 82 and an outlet 15 through which more or less alkaline water is available for washing purposes etc. This outlet is of course optional and not be present in all embodiments of the invention, since if the alkaline water is not needed it may be drained through the conduit 81.

A polarographic sensor S1 for sensing of the of the ozone concentration is preferably arranged at the outlet from the tank, or in an outlet conduit 84 from the tank 60. It could also be arranged in the tank 60.

The ozone sensor may of course be of any kind which would suffice for the intended use. In this specific embodiment a ozone sensor available from Toa Electronics, Tokyo, Japan.

At or near the upper part of the tank an outlet conduit 72 is arranged having a check valve BV2 for hindering a vacuum from forming when the tank is emptied. The check valve could of course also be magnetically controlled. A branch conduit 73 is arranged in the conduit 72 between the tank 60 and the check valve BV2. In the conduit 73 a spring loaded valve BV3 is arranged, which ensures that a constant pressure is upheld in the tank 60 until some or all of the content of the tank 60 is emptied.

After the ozone-generator a controlled three-way valve V3 either leads the produced ozone to a mixing chamber BK via a conduit 75, in which a check valve BV4 is situated in order to stop the flow running backwards in the conduit 75, or leads the produced ozone out from the system via conduit 76.

When the level indicator indicates that the predetermined level of the water in the tank 60 has been reached the valve V1 is closed. The valve V2 opens the supply of oxygen to the ozone generator. The oxygen flow passes the pressure sensor PR and the flow sensor F1. The ozone generator according to the embodiment comprises a voltage/frequency converter, which is coupled to an electrode, which is placed in an air cooled chamber. When the oxygen passes the electrode ozone is produced. Important parameters for optimal production of ozone is flow velocity of the oxygen over the electrode and the effect of the generator.

There are preferably two circulatory paths for the ozone-mixed water in the system. The first one comprises a branch conduit 77 which is arranged at the lower part of the tank 60 leading the ozone water solution to a pump P1 and back into the tank 60. The pump continuously circulates the water from the tank 60 to the mixing chamber BK and back to the tank.

Near the bottom of the tank 60 a conduit 84 is arranged which leads to a controlled valve V4.

The controlled valve V4 may either let the ozone-water solution leave the system through an ozone-water outlet 12 or recirculate the solution preferably to the upper part of the tank 60 through a conduit 78.

The produced ozone gas flows via the valve V3 and the conduit 75 and a check valve BV4 to the mixing chamber BK, where the produced ozone gas is mixed with the water pumped by the pump P1 from the tank 60 via conduit 77. The chamber comprises according to the invention a combination of a diffuser, which creates a turbulent water flow and porous member through which the gas comes into contact with the water, this member is e.g. a sintered atomising gas nozzle, (below called nozzle or gas nozzle), preferably made from acid-proof material having a pore size of 0.2–10 microns. The mixing sequence continues until the predetermined ozone concentration in the tank 60 has been attained The mixing chamber is described further in concentration with FIG. 4.

The ozone concentration is preferably measured by polarography by the sensor S1 at predetermined intervals. In other embodiments other types of sensors may be used as would be obvious to the man skilled the art.

As soon as the concentration falls below a predetermined minimum value the sequence for preparing the ozone water is repeated. By pumping the ozone-water solution from the tank through the conduit 77 via the pump P1 and the mixing chamber BK and thereafter back to the tank it is ensured that the concentration of the ozone-water be kept at the predetermined value at all times.

The conduit 77 when returning the water to the tank preferably enters ozone-enriched water coming from the mixing chamber BK below the level if the liquid in the tank.

When ozone-water is not withdrawn from the tank for some time the ozone concentration is very slowly declining. The pump P2 is used to create a circulatory movement of the ozone-water past the ozone concentration measuring sensor and through the tank by pumping the ozone-water from the bottom of the tank via the valve V4 back to the tank 60 returning the ozone-water to the upper part of the tank.

Surplus of ozone is allowed to pass out through the check valve BV3 to a converter 25. In the converter the ozone is converted catalytically to oxygen and thereafter allowed to exit from the system via an outlet 26 from the converter 25 and any liquid formed during the process may be drained through the conduit 27.

Drawing off the ready-made solution, the active water, from the tank is accomplished in this embodiment by opening the magnetic valve V4 and letting the pump P2 empty the tank 60. In doing so the valve BV2 prevents a vacuum from forming in the tank.

From the system there is also a possibility to discharge ozone in the form of gas through the three-valve V3 depending on if ozone in the form of gas is needed for the specific application at hand.

A control system (PLC) is arranged in order to control e.g. the valves and parameters, such as temperature, and the level in the tank the generation of ozone, the filtering of the water and the mixing of ozone and water and the release of ozone of ozone-water (active water) from the system.

Figure 3:
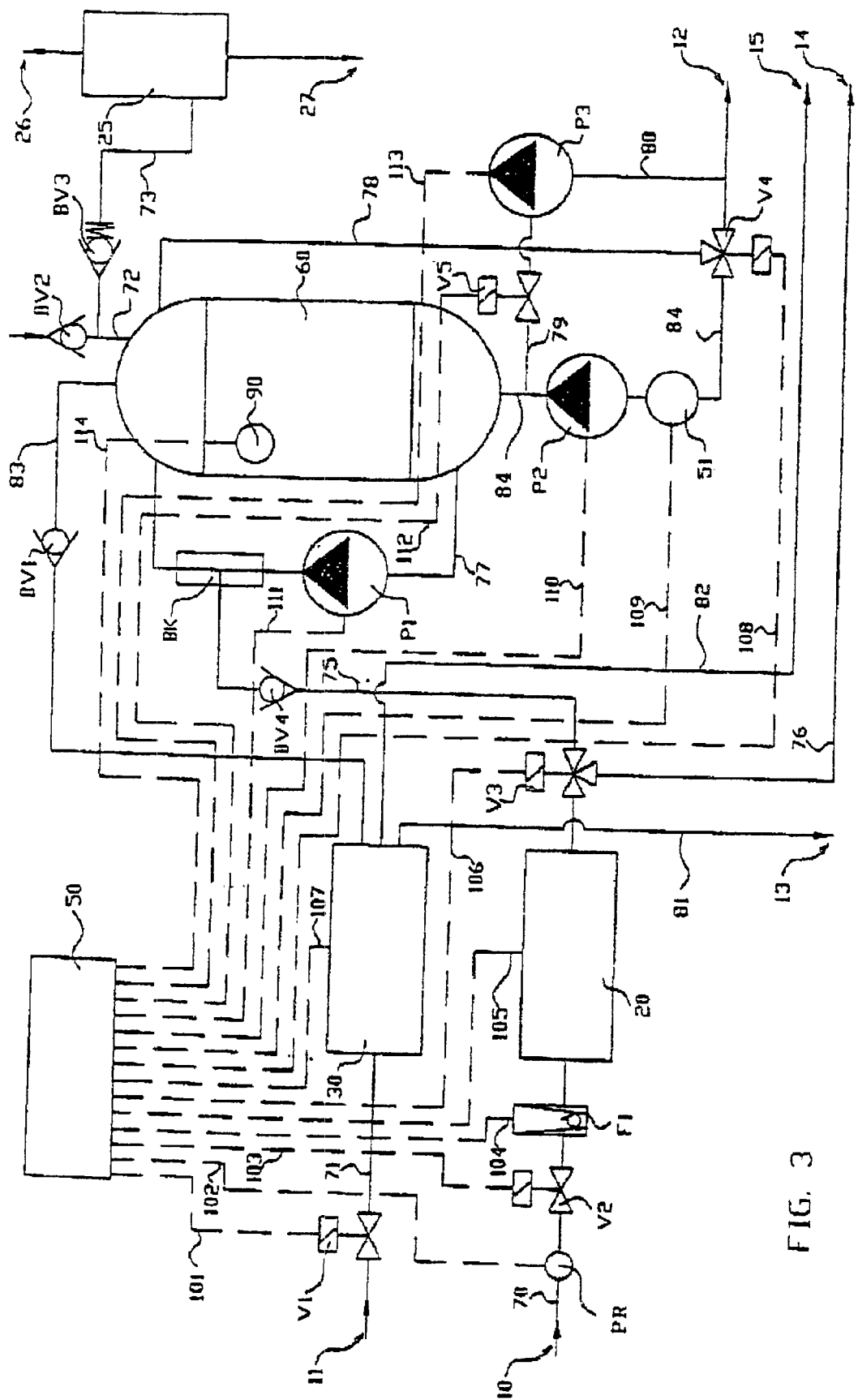
FIG. 3 shows a schematic overview of the control system of one embodiment of the mixing chamber according to the invention.

An example of an arrangement of a control system to be used in the method and the device according to the above described embodiment is shown in FIG. 3.

To be noted is that the embodiment according to FIG. 3 comprises an extra pump P3 compared to the embodiment in FIG. 2 for withdrawal of active water via a branch conduit 79 before the pump P2. In the branch conduit 79 a controllable valve V5 is arranged before pump a P3. A conduit 80 connects the outlet from the pump P3 with the ozone-water outlet 12. This extra pump and conduit is added to allow for a faster flow from the tank 60.

The control system comprises a control unit 50, one or more control programs (ex. of control program sequences below), A/D-converters, processing means, input and outputs means for analogue and/or digital signals and/or control signals. In this embodiment there are 14 leads for controlling valves in dependence of the control program and of measured parameters, such as temperature, flow, concentration, etc.

The control unit 50 may be controlled manually from a control panel (not shown). Using the panel different sequences may be chosen depending on the type of application the system is used in. The parameters of the chosen control sequence program preferably relate to empirical values.

The unit 30 for treatment of incoming water (filtering and demineralizing) uses the following signals: on/off, stepwise pH-adjustment, flushing of the electrolysis chamber (not shown) of the unit 30, and possibly control and adjustment of the water temperature.

The ozone generator 20 uses the following signals: off/on, stepwise power control (the electrode potential).

The ozone sensor 51 and the circuitry thereof generates an analogue A/D-signal which is used in the chosen control sequence.

The control unit 50 controls valves and pumps and receives signals depending on sensed or measured parameters all in dependence of the chosen sequence. Signals on lead 101 controls the incoming water by means of the valve V1. Signals on lead 102 measures the pressure the incoming air/oxygen by means of the pressure gauge PR. Signals on lead 103 controls the valve V2. Signals on lead 104 controls/measures the incoming air/oxygen flow by means of the flow meter F1. Signals on lead 105 controls the ozone generator unit 20. Signals on lead 106 controls the incoming air/oxygen by means of the three-way valve V3. Signals on lead 107 controls the filtering and demineralizing in the unit 30 for treatment of water. Signals on lead 108 controls the active water in the recirculation measuring circuit by means of the valve V4 and the release of the ozone-water solution (active water) from the system. Signals on lead 109 from the ozone sensor 51 are used for controlling the process.

Signals on lead 110 controls the pump P2, on lead 111 controls the pump P1, on lead 112 controls the valve V5, on lead 113 controls pump P3 and on lead 114 signals from the liquid level indicator 90 is passed to the control unit.

In FIGS. 4a and 4b is shown an embodiment of a mixing chamber according to the invention. The numbers used for details in FIGS. 4a and 4b correspond to each other. In FIG. 4a the chamber is shown from the outside displaying an inlet 1 for water and one inlet 2 for ozone and an outlet 3 for the water/gas solution. The inlet 1 for water and the outlet 3 are connected by means of an inner conduit 9 in the form of a bore or the like. In FIG. 4b the same chamber is shown in another view and partly in section. From the ozone inlet 2 the ozone enters a central bore 6 in the nozzle 5, which bore 6 has a dead-end. The ozone will thus have to migrate through the nozzle 5 and enter the flow of water outside the nozzle. Thus the gas is dispersed in the form of very fine bubbles in the water in the chamber using the atomisation nozzle according to the invention. The nozzle is preferably made from sintered ceramics or stainless steel.

An important factor in choosing the material in the mixing chamber is that a material is chosen, which, if possible, is inert to ozone and which does not show any catalytic effect on the decay of the ozone. In order to achieve a good mixing of the ozone gas with the water it is essential that the gas is atomized by means of the sintered atomising nozzle or any other injection means giving the same effect.

In FIGS. 5a, 5b, and 5c three further embodiments of the mixing chamber according to the invention are shown schematically. The numbers used for details common to FIGS. 5a, 5b, and 5c correspond to each other. In the figures the following is shown denoted by corresponding numbers: inlet 1 for water, inlet 2 for ozone, and outlet 3 for the water/gas solution.

In FIG. 5a a nozzle 5 is arranged in an inner conduit 9 between a water inlet 1 and an ozone-water outlet 3. The nozzle exhibits a central through-bore 7 through which the water passes from the inlet to the outlet. The nozzle is arranged such that all the water has to pass through the bore 7. The ozone inlet 2 comprises a conduit which ends in a chamber 8 sealed off from the water conduit by the nozzle as such making sealing contact with the conduit walls. The chamber 8 is filled with ozone which migrates through the nozzle into the water passing from the inlet 1 to the outlet 3 through the central through-bore 7. The through-bore preferably exhibits a smaller cross-section area halfway through the bore than at the two ends thereof.

In FIG. 5b a nozzle 5 is arranged in an inner conduit 9 between a water inlet 1 and an ozone-water outlet 3. The nozzle exhibits a central blind bore 6 through which ozone gas enters from the ozone inlet 2. The nozzle is arranged across the conduit 9. The water will thus have to pass by the nozzle 5 where the ozone will mix with the water. The conduit 9 is designed such as to give as much free area of the nozzle contact with the passing water, while still providing a constriction in the conduit. This is clearly seen from the cross-section B—B in FIG. 5b.

In FIG. 5c a nozzle 5 is arranged in an inner conduit 9 between a water inlet 1 and an ozone-water outlet 3. The conduit 9 is arranged to make a 90° turn where the ozone inlet emerges into the conduit 9. The nozzle exhibits a central blind bore 6 through which ozone enters from the ozone inlet 2. The nozzle is arranged in the conduit 9 such that the water from the inlet will pass on the outside of the nozzle 5 along most of the nozzle outside area as to give as much contact with the passing water, while still providing a constriction in the conduit.

Examples of control program sequences is given below to illustrate the functioning of the system.

A control program sequence for cleaning/sterilising of a medical instrument may be performed accordingly:

A chamber (not shown) adapted to the medical instrument is connected to the system. The outlet from the chamber is connected via the converter system to a drain. The converter system may of course be a separate one if so is desired.

Two embodiments of subsystem for sterilisation is describe in conjunction with FIG. 9 and FIG. 10 in which measurements are made in order to ensure that set goals are attained.

When the on-button is pressed on the instrument panel the valve V1 receives a signal opening the water supply to the system. At the same time the water treatment unit 30 is given a signal to regulate the pH-value of the water. Water having different pH-values may be separated in the unit. Water having a low pH-value is directed to the tank 60 and the water having a high pH-value, alkaline water, is directed to the chamber for a first cleaning of the instrument.

When the liquid level indicator 90 signals that the predetermined liquid level in the tank 60 has been attained a signal is given to V1, which closes.—The pressure gauge indicates that (air/)oxygen is present—a signal opens V2 and the ozone generation on the ozone generating unit 20 is initiated by a signal from the control unit 50 (control system 100)—pump 1 is started by a signal—pump P2 is started by a signal. The mixing of ozone and water is continued until e.g. 5 ppm has been attained in the solution—a closing signal is sent to V2, and signals are sent to P1 and the ozone generator to stop—signals are sent by the control sequence program to open the valve V5 and start pump P3 (high flow) and the active water is pumped into the chamber for e.g. 10 sec.–V5 is closed and P3 is stopped—a signal opens V4 (low flow) to the chamber for e.g. 4 min. Thereafter the controlled valves V2 and V3 are opened by the control program sequence and the ozone generator unit 20 is given a signal to start producing ozone, and ozone gas is allow to flow through the chamber during e.g. one minute. This sequence may be repeated trice.

It is within the field of the invention to provide control leads and control functions within the control program sequence for controlling valves, pumps, brushes etc. of the chamber.

A control program sequence for filling of spray bottles, which spray may be used for i.a. disinfectant uses may be performed accordingly:

A spray bottle holder (not shown), for one or several bottles is connected to the outlet from the system. On the on-signal the valve V1 is given a signal opening the valve and thereby providing water to the system. At the same time the water treatment unit 30 is given a signal to regulate the pH of the water. Water having a low pH fills the tank 60, and the alkaline water is drained from the system. As the liquid level indicator 90 sends a signal to the control unit the valve V1 is closed—it is controlled that the pressure gauge PR indicates presence of air/oxygen—the valve V2 is given a signal to open and the ozone generator unit 20 is given a signal to start generating ozone—the pump P1 is given a start signal—the pump P2 is given a start signal. The admixture of ozone into the water is started, and is stopped when the concentration measured in the water from the tank reaches 2 ppm—the valve V2 is closed and the ozone generating unit 20 and the pump P1 are stopped—if and when the ozone concentration declines below 1.5 ppm, the ozone admixture sequence is repeated.

The concentration of the ozone-water solution is controlled by the predetermined value, represented by programmable variables in the sequence.

When the spray bottle is to be used it is place in the spray bottle holder—the bottle is emptied from any water therein.—The valves V2 and V3 are given signals to open, the ozone generator unit 20 is given a signal to start generating ozone and the bottle is flushed with ozone, it could of course also be flushed with the ozone-water solution. A push button for filling acts on the valve V5 and the pump P3, which fills the bottle—the filling of the bottle may for instance be time control, other possibilities are within the reach of the man skilled in the art. When the bottle has been filled a safety check may be made on the water in the bottle or in connection with the filling of the bottle e.g. in connection with the outlet from the system. If the ozone connection is too low an alarm will preferably be activated indicating that the concentration of ozone in the bottle is too low.

A procedure for the water treatment in the unit 30 and in connection with this may be performed accordingly.

Tap water, possibly from the municipal water supply, is purified using e.g. an active carbon filter. Particles of rust, chemicals organic martial, paint etc. is absorbed in the filter. The service life of the filter may be controlled by the setting of a time limit.

The water purified in the filter is thereafter passed through an electrolysis cell (not shown), which is constructed from platinum/titanium and SUS-316 acid-proof steel. By choosing the appropriate material an optimal electrolysis of the water is attained. The electrolysis cell is preferably cleaned each 10 minutes during app. 30 sec.

By electrolysis of the water ions are separated such that some are guided to the positive electrode and some to the negative electrode. The positive ions directed to the negative electrode gives alkaline water and the negative ions directed to the positive electrode give acid water. In the exemplary system discussed above the water from the positive electrode (acid water). This fraction of the water is used to make ozone-water solutions having different degrees of concentration. There is also a possibility for use of the alkaline water coming from the negative electrode for specific applications.

The requirements as to the water used are that the temperature preferably should be within the interval 5° C.–10° C., the conductivity of the treated water should preferably be <80 $\mu$S/cm, the water should display the quality called soft water, and the preferred pH-interval is 2–4 pH units.

By using tap water from a municipal source or the like higher concentrations of $Cl^-$, $S^-$, and $P^-$ are attained. This results in a lower pH and better conditions for dissolving ozone in the water. The ozone-water solution according to the invention will be more stable in a solution having a low pH.

An application in which the apparatus/system according to the invention may be used is a method for measuring the amount of organic contaminants in a liquid. This application requires that the ozone concentration in the ozone gas is closely regulated.

The invention also resides in feeding ozone gas of a determined concentration to a, preferably closed, container in which the liquid having organic contaminants therein is kept. The feeding of ozone gas to the container results in reaction between the contaminants and the ozone. As long as there are contaminants in the container the ozone will be spent by reaction. This implies that as long as there are contaminants in the receiver no ozone will be possible to detect in the container. Respect must also be paid to the natural decay of the ozone.

Other parameters having influence on the measurements of the above type is contact time, temperature, ozone gas concentration, the material in the container as such and the type of contamination and the concentration of the same. These and other parameters to be evaluated in the separate instance are to be taken into account in the measurements as to reaction speed and the expected end result.

Experiments were undertaken in order to make certain the influence of certain variables on the results and to validate the effect of the ozone-water.

In FIG. 6 a flow-cell is shown which was used in the experiments described below. The results are shown in FIGS. 7a and b.

The aim of the experiments were to show the sterilizing effect of the ozone-water-solution according to the invention. Two concentrations were used, 3 and 6 mg/l, resp. The organisms studied as examples of such were *Bacillus Cereus* and *Staphylococcus aureus* on glass surfaces.

*Bacillus Cereus* is patogenous and also a common cause to the destruction of food products. In their spore form they are resistant towards drying out, high temperatures, and chemicals.

*Staphylococcus aureus* is a Gram-positive coccus which does not have a spore form but still is very resistant towards drying out and different chemicals. It forms toxins and can cause food poisoning.

Materials and Methods:

The methods used in these experiment is in accordance with the methods and experiences the SIK (Institutet för Livsmedel och Bioteknik, Gothenburg, Sweden). Respects has also been taken to the methods for validation of disinfectants, which are being established by the technical committees within the EU. Here is referred to the work done by TC216. The Bacteria were fastened and dried on hydrofobic glass surfaces. They were exposed to ozone-water during determined time periods and thereafter the number of surviving bacteria was analyzed.

Micro-organisms:

Spores from two different strains of *B. Cereus* were used. The so called strain (ATC 14579, SIK 229) and a strain isolated from butter from a dairy (SMR 781, SIK 341). Vegetative cells of *Staphylococcus aureus* (ATCC 6538, SIK 295) were also used.

The glass surfaces and the preparation of these:

The glass surfaces used were microscope slides, which by treatment with methyl silane where rendered hydrophobic.

Bacillus spores and the Staphylococcus were suspended in a physiologic salt solution in a concentration of $10^7$ to $10^8$ macro-organisms/ml. The slides were suspended in this solution for an hour. Meanwhile the macro-organisms fastened onto the surfaces. The slide were rinsed with distilled water and dried in room temperature for about 12 hours.

In order to provide the ozone-water a system was used comprising an ozone-generator of the type Ozonize. This unit uses a plasma resonance electrode. Oxygen was used to generate ozone, which cuts the development of $NO_x$-gases considerably.

In order to have pure water of uniform quality de-ionized water, Kenmityl T-vatten, was used.

The ozone-water solution was prepared according to the invention using a device, which is shown in FIG. 4 by a technique we have named "Diffu-Z-ektor-technic". This technique is a combination of diffusion and injector technique. This technique gives a controlled gas and water flow.

The slides 101 were mounted in a flow cell 102 shown in FIG. 6,. The ozone-water was passed through the flow cell, from the inlet 103 to the outlet 104. The flow in the cell was at this occasion 0,1 l/min. To continuously control/monitor the concentration of the concentration of the dissolved ozone of the water passing in and out of the flow cell a pornographic membrane electrode TOA was used. The measurement instrument was connected both to the inlet and the outlet from the flow cell. Two concentrations of ozone in the water was used, 3 mg/l and 6 mg/l.

The validation of surviving micro-organisms:

The reference values—i.e. the number of bacteria per slide before exposition to the ozone-water was enumerated using swab-technique. The surfaces were swabbed using an alginate swab and smear was made on TGE-plates (Trypton Glykos Extract Agar).

The values after exposition were measured by form-molding nutrient agar (Trypton Soya Agar) having an admixed color indicator (Tetrazolium Chloride) over the bacteria on the slide in near connection to the exposition for the ozone-water.

Results and Discussion:

The results are represented in Table I and shown in FIGS. 7a and 7b. From these diagrams, 7a representing the test run using a concentration of 3 ppm ozone and 7b a the test run using a concentration of 6 ppm ozone, there can be seen no logical differences between the specimens treated during 5, 10, and 15 minutes. This may be understood such that there is an almost instantaneous or at least a very fast action of the ozone-water and that after 5 minutes only remains a so called tail, i.e. after 5 minutes the survival speed remains constant.

One difference may be noted in that the higher concentration of ozone gives a better effect. The noted logarithmic reductions for the two strains of Bacillus and for the Staphylococcus was app. 2 logarithmic units for 3 ppm and 3 logarithmic units for 6 ppm. the Bacillus strain was the most resistant.

TABLE 1

| | CFU = colony forming unit | | | | | |
|---|---|---|---|---|---|---|
| | 229 *B. cereus* typestrain | | 341 *B. cereus* dairystrain | | 295 *S. aureus* | |
| Treatment | Measured CFU value | Average ± SD | Measured CFU value | Average ± SD | Measured CFU value | Average ± SD |
| Initial value | $2.6 \times 10^3$ | $1.8 \times 10^5 \pm$ | $1.4 \times 10^5$ | $6.0 \times 10^5 \pm$ | $17.0 \times 10^3$ | $8.4 \times 10^3 \pm$ |
| | $3.4 \times 10^5$ | $1.2 \times 10^5$ | $1.1 \times 10^6$ | $3.8 \times 10^5$ | $2.0 \times 10^3$ | $8.0 \times 10^3$ |
| | $0.7 \times 10^5$ | | $1.0 \times 10^6$ | | $5.0 \times 10^3$ | |
| | $0.04 \times 10^5$ | | $8.5 \times 10^5$ | | $17.0 \times 10^3$ | |
| | $1.8 \times 10^5$ | | $4.0 \times 10^5$ | | $1.0 \times 10^3$ | |
| | $2.0 \times 10^5$ | | $3.0 \times 10^5$ | | | |
| | | | $3.9 \times 10^5$ | | | |

TABLE 1-continued

CFU = colony forming unit

| | 229 B. cereus typestrain | | 341 B. cereus dairystrain | | 295 S. aureus | |
|---|---|---|---|---|---|---|
| Treatment | Measured CFU value | Average ± SD | Measured CFU value | Average ± SD | Measured CFU value | Average ± SD |
| 3 ppm 5 min | 0 | 43 ± 51 | 200 | 408 ± 520 | 2 | 2 ± 1.6 |
| | 30 | | 25 | | 3 | |
| | 100 | | 1000 | | 0 | |
| 3 ppm 10 min | 100 | 100 ± 0 | 500 | 533 ± 451 | 10 | 503 ± 495 |
| | 100 | | 100 | | 1000 | |
| | 100 | | 1000 | | 500 | |
| 3 ppm 15 min | 25 | 50 ± 25 | 1000 | 1000 ± 0 | 2 | 18 ± 28 |
| | 50 | | 1000 | | 50 | |
| | 75 | | 1000 | | 1 | |
| 6 ppm 5 min | 0 | 0 ± 0 | 25 | 25 ± 0 | 3 | 13 ± 15 |
| | 0 | | 25 | | 5 | |
| | 0 | | 25 | | 30 | |
| 6 ppm 10 min | 15 | 7 ± 7.2 | 25 | 142 ± 142 | 8 | 9 ± 1 |
| | 5 | | 300 | | 9 | |
| | 1 | | 100 | | 10 | |
| 6 ppm 15 min | 0 | 0 ± 0 | 500 | 192 ± 267 | 2 | 2 ± 1 |
| | 0 | | 50 | | 1 | |
| | 0 | | 25 | | 3 | |
| 6 ppm 1 min | 28 | — | 100 | — | — | — |
| Gas 30 min | 1 | — | 10 | — | 0 | — |

In a second test run shown in FIG. 8 the effect of the zone solution according to the invention is shown on two different bacteria: *Feacal streptococcus* and *Pseudomonas aeruginosa*. The analysis was performed by Vattenvardslaboratoriet VVL, Stockholm, Sweden.

The bacteria were inactivated by a 1 ppm ozone water solution and the results in table 2 were obtained.

TABLE 2

| Bacteria | cfu before treatment | cfu after treatment |
|---|---|---|
| *Feacal streptococcus* | 88 | 0 |
| *Pseudomonas aeruginosa.* | 66 | 0 | cfu = concentration of bacterias/ml

This clearly shows the effect of the ozone water according to the invention.

The examples in the description has been given in order to demonstrate and clarify the system and the method for production of the ozone water and the ozone water according to according to the invention and should not be considered limiting the scope of the invention.

The water prepared according to the method according to the present invention is useful in several aspects. It may be used in a method for detection of bacteria or other living matter, specially contaminating material. The method comprises supplying water, having dissolved ozone therein of a known concentration to an object, measuring the ozone concentration in said water as said water is removed from the object, and thereafter measuring the difference in concentration between the water supplied and the used water. As the ozone is consumed by the contaminating material present the difference in concentration may be used as a measure of the amount of bacteria or other living matter present on or in said object. This may be accomplished e.g. by means of a container having an inlet for said water containing ozone of a predetermined concentration and an outlet for said water. At the outlet from the container an ozone concentration measurement means is arranged. Control means are preferably arranged to control the measurement method automatically.

A further use of the water prepared according to the invention is the use of said water containing ozone having a predetermined concentration of ozone for destruction of cells, e.g. cancer cells. This may be accomplished on account of the sensitivity of abnormal cells e.g. cancers cells being more sensitive to ozone than normal cells. In order to accomplish this, a device may be used which comprises means for selectively distributing the water comprising ozone dissolved therein, means for controlling the amount of said water distributed and also means for removal of not-spent water so as to avoid excessive contact between the water and normal cells. The device preferably also has an automatic control system.

In FIG. 9 is shown a detector and purification subsystem according to the invention to be used with or integrated in the system according to the invention. From the system for production of ozone-water or ozone described above ozone-water or ozone gas entering an inlet 901 is allowed to pass through conduit 902. The gas thereafter passes by a sensor 910 for measuring ozone concentration and/or ozone amount passing into the subsystem. The sensor 910 may be left out and the values from the sensor (51) of the main system may be used instead. The ozone-water or ozone gas thereafter follows a conduit 903 and enters a treatment chamber 912, which may be a chamber containing utensils to be sterilised or in itself comprise an apparatus, such as a dialysis apparatus or the like. The subsystem must in the latter case be provided with connections for sealingly attaching the apparatus. The used ozone-water or ozone gas exits the chamber via a sensor 911 and from there to destruction of the ozone or the like via a conduit 905. A processor/measurement unit 913 controls the two sensors and their respective values via conductors 920 and 921.

If the sensor 910 indicates a higher measurement value than the sensor 911 this shows that the ozone is consumed by some organic matter such as bacteria. When there is balance between the two measurements indication is given that the utensils in the chamber 912 or the unit 912 is disinfected.

In FIG. 10 another embodiment of the above subsystem is shown. In this subsystem only one sensor is used.

From the system for production of ozone-water or ozone described above ozone-water or ozone gas enters an inlet 1001 and passes through a conduit 1002 and passes by a three-way valve. The ozone-water or ozone gas thereafter either follows a conduit 1003 and enters a treatment chamber 1012, which may be a chamber containing utensils to be sterilised or in itself comprise an apparatus, such as a dialysis apparatus or the like. The used ozone-water or ozone gas exits the chamber via a conduit 1004 having a three-way valve and passes a sensor 1011 for measuring ozone concentration and/or ozone amount passing out from the subsystem and from there to destruction of the ozone or the like via a conduit 1005.

In order to measure contamination, control disinfecting result etc. the ozone gas or the ozone-water is in turns led via conduit 107 thereby bypassing the unit/chamber 1012.

A processor/measurement unit 1013 controls the sensor 1011 and the two 2-way valves via conductors 1021, 1022, and 1023 in the same manner as in FIG. 9.

What is claimed is:

1. A system for production of water having ozone dissolved therein, said system comprising:

a water feeding means (11,V1,71,30,83), a container means (60), an ozone feeding means (10,70,V2,F1,20) for feeding ozone to a mixing means (BK) for dissolving ozone in said water, said mixing means (BK) drawing water from a lower output of the container (60), ozone measuring means (51) for measuring the ozone concentration of said water in the container (60), water pumping means (P1, P2) for circulating said water from the lower part of the container (60) to the upper part of the container (60) in dependence of a measured ozone concentration in said water and said ozone feeding means feeding ozone to said mixing means (BK) in dependence of a predetermined ozone concentration value, said container (60) having an outlet (84,P2,84, V4,12) for water having the predetermined concentration of ozone, said system adapted to maintain a predetermined liquid level in said container, said system further comprising a control unit (50) for controlling the system in dependence of measured physical parameters in the system.

2. A system according to claim 1, characterized in that a conduit (77) is adapted to return the water having ozone dissolved therein from said mixing means (BK), to a point in the container (60) below the liquid level in said container (60).

3. A system according to claim 1 or 2, wherein said water feeding means (11,V1,71,30,83) comprises:

means (V1) for controlling the flow of water to the system and a filtering and de-mineralizing unit (30).

4. A system according to claim 3, wherein said ozone feeding means (10,70,V2,F1,20) comprises:

means (V2) for controlling the flow of oxygen gas and/or air to the system, an ozone generator, and means (V3) for distributing the flow of ozone gas to the mixing means (BK), or to an outlet for ozone gas (14), a pressure sensor (PR), and a flow sensor (F1).

5. A system according to claim 4, wherein said mixing means (BK) comprises:

a chamber having a water inlet (1) for water from the lower part of said container (60), an ozone inlet (2) for ozone from said ozone feeding means, said ozone inlet (2) having a diffusor means comprising a porous member, preferably exhibiting a pore size of approx, 0.2–10 microns, a water outlet (3) for water having dissolved ozone through an outlet conduit leading to the upper pan of the container (60), wherein there are control means for monitoring the addition of ozone in dependence of the measured ozone concentration.

6. A system according to claim 5, characterized in that the ozone concentration measuring means (51) is arranged in the outlet conduit (71) from the lower part of the container (60), pumping means (P2) provided to withdraw said water from the bottom of the container (60) past the concentration measuring means (51) and in dependence of a control signal from the control unit (50) either return the water to a point below said predetermined liquid level in the container (60) or to deliver said water through the outlet (84,P2,84,V4,12) for water having the predetermined concentration of ozone.

7. A mixing device for establishing a liquid-gas mixture, comprising:

a liquid inlet (1), a gas inlet (2) and a liquid-gas mixture outlet (3), and a conduit (9) for joining said liquid inlet (1) and said liquid-gas mixture outlet (3), characterized by a porous member (5), at least at the upstream end of the porous member (5) being in scaling contact with the inner walls of said conduit (9), said porous member (5) having a first surface being in contact with the liquid and second surface being in contact with the gas, the dimensions of said conduit (9) being such that a pressure difference is created in the liquid before and after said member (5) such that the gas is made to diffuse through said porous member (5), characterized in said porous member (5) exhibiting a through-bore (7) essentially co-axial with said conduit (9), the bore (7) constituting a constriction of the conduit (9), the inside walls of said through-bore (7) constituting said first surface, said inner wall having an essentially circumferential recess formed in the inner walls of the conduit essentially along the porous member (5) said recess connected with the gas inlet (2) giving the gas access to the outside of the porous member, said outside constituting said second surface.

8. A mixing means according to claim 7, characterized in said porous member (5) exhibiting a blind-bore (7), the blind-bore (7) communicating with the gas inlet (2), the inside walls of the blind-bore (7) thus constituting said second surface, the outer surface of the porous member (5) constituting said first surface in contact with the liquid, said porous member (5) constituting a constriction of the conduit (9).

9. A method for production of active water, water having dissolved ozone therein, characterized by the following steps:

feeding filtered and de-mineralized water to a container to a predetermined level;

re-circulating the water from the bottom of said container through a conduit comprising pumping means and mixing means;

dissolving ozone gas in said re-circulated water in said mixing means under controlled inlet flows;

feeding said water having dissolved ozone to said container, measuring the instant ozone concentration of said water having dissolved ozone;

said water having dissolved ozone re-circulated through the mixing means under addition of further ozone in dependence of said measurement of the ozone concentration;

said last step repeated when the measured ozone concentration is below a predetermined value.

10. A method according to claim 9, characterized by said method also comprising the step of re-circulating the water having dissolved ozone through a separate conduit in which the ozone concentration measurements are made and from which conduit withdrawal of the water having the predetermined concentration of ozone can be done.

11. A method according to claim 9 or 10, characterized by the water used being used according to the method being filtered and de-mineralized such that the water exhibits a conductivity preferably <80 $\mu$S/cm.

12. A method according to claim 11, characterized by the water used being used according to the method being filtered and de-mineralized such that the water exhibits a quality called soft water, and the preferred pH-interval is 2–4 pH units.

13. A method for detection of bacteria or other living matter comprising the step of supplying water, having dissolved ozone therein of a known first concentration, said water prepared according to claim 12, to an object, measuring the ozone concentration in said water as said water is removed from the object to determine a second concentration, the difference between the first and second concentration being a measure of the amount of bacteria or other living matter present on or in said object.

14. A subsystem for production of water having ozone dissolved therein, said system comprising:

water feeding means (11, V1, 71, 30, 83) having means (V1) for controlling the flow of water to the system and a filtering and de-mineralizing unit (30), a container means (60), ozone feeding means (10, 70, V2, F1, 20) having means (V2) for controlling the flow of the oxygen gas and/or air to the system, an ozone generator, and means (V3) for distributing the flow of ozone gas to the mixing means (BK), or to an outlet for ozone gas (14), a pressure sensor (PR) and a flow sensor (F1), for feeding ozone to a mixing means (BK) having a chamber having a water inlet (1) for water from the lower part of said container (60), an ozone inlet (2) for ozone from said ozone feeding means, said ozone inlet (2) having a diffusor means comprising a porous member, a water outlet (3) for water having dissolved ozone through an outlet conduit leading to the upper pan of the container (60), whereat there are control means for monitoring the addition of ozone independence of the measured ozone concentration, for dissolving ozone in said water;

said mixing means (BK) drawing water from the lower part of the container (60) by way of a conduit (77) that is adapted to return the water having ozone dissolved therein from said mixing means (BK), to a point in the container (60) below the liquid level in said container (60), ozone measuring means (51) that is arranged in the outlet conduit (71) from the lower part of the container (60), hat pumping means (P2) are provided to withdraw said water from the bottom of the container (60) past the concentration measuring means (51) and in dependence of a control signal from the control unit (50) either return the water to a point below said predetermined liquid level in the container (60) or to deliver said water through The outlet (84, P2, 84, V4, 12) for water having the predetermined concentration of ozone, for measuring the ozone concentration of said water in the container (60), water pumping means (P1, P2) for circulating said water from he lower par of the container (60) to the upper part of the container (60) in dependence of a measured ozone concentration in said water and said ozone feeding means feeding ozone to said mixing means (BK) in dependence of a predetermined ozone concentration value, said container (60) having an outlet (84, P2, 84, V4, 12) for water having the predetermined concentration of ozone, said system adapted to maintain a predetermined liquid level in said container, said system also comprising a control unit (50) for controlling the system in dependence of measured physical parameters in the system, in conjunction with a mixing means to be used preferably with active water having ozone dissolved therein, said water system characterized by a treatment chamber (912; 1012) or detachable connections for connecting an apparatus or device to be treated with the ozone-water mixture, at least one ozone sensor (910, 911; 1011), means for registering and control at least of the ozone content of the ozone-water mixture after said mixture has flown through said treatment chamber (912; 1012) or said apparatus or device to be treated.

15. A subsystem according to claim 14, characterized in a second ozone sensor being present after the outlet from the container of the system and before the treatment chamber (912; 1012) or detachable connections for connecting an apparatus or device to be treated with the ozone-water mixture, said sensor used for correlation of the ozone content of the ozone-water mixture before and after the treatment chamber (912; 1012) or detachable connections for connecting an apparatus or device.

16. A method of using a subsystem according to claim 15, characterized in that the used ozone water is water having ozone dissolved therein is produced by the following steps: feeding filtered and de-mineralized water to a container to a predetermined level; re-circulating the water from the bottom of said container through a conduit comprising pumping means and mixing means;

dissolving ozone gas in said re-circulated water in said mixing means under controlled inlet flows;

feeding said water having dissolved ozone to said container, measuring the instant ozone concentration of said water having dissolved ozone;

said water having dissolved ozone re-circulated through the mixing means under addition of further ozone in dependence of said measurement of the ozone concentration;

said last step repeated when the measured ozone concentration is below a predetermined value.

17. A method according to claim 16, characterized in that the ozone water production also comprising the step of re-circulating the water having dissolved ozone through a separate conduit in which the ozone concentration measurements are made and from which conduit withdrawal of the water having the predetermined concentration of ozone can be done.

18. A method according to claims 16 or 17, characterized in the water used for producing the ozone water being used according to the method being filtered and de-mineralized such that the water exhibits a conductivity <80 $\mu$S/cm.

19. A method according to claim 18, characterized in the water used for producing the ozone water being used according to the method being filtered and de-mineralized such that the water exhibits a quality called soft water.

* * * * *